United States Patent
Lee

(10) Patent No.: US 9,215,934 B2
(45) Date of Patent: Dec. 22, 2015

(54) CORRECTIVE CHAIR USING SLIDER MEANS

(71) Applicant: Jae Hyun Lee, Jeollabuk-do (KR)

(72) Inventor: Jae Hyun Lee, Jeollabuk-do (KR)

( * ) Notice: Subject to any disclaimer, the term of this patent is extended or adjusted under 35 U.S.C. 154(b) by 0 days.

(21) Appl. No.: 14/352,965

(22) PCT Filed: Oct. 17, 2012

(86) PCT No.: PCT/KR2012/008477
§ 371 (c)(1),
(2) Date: Apr. 18, 2014

(87) PCT Pub. No.: WO2013/058538
PCT Pub. Date: Apr. 25, 2013

(65) Prior Publication Data
US 2014/0246890 A1   Sep. 4, 2014

(30) Foreign Application Priority Data
Oct. 21, 2011   (KR) .......................... 10-2011-0107842

(51) Int. Cl.
*A47C 1/00*   (2006.01)
*A47C 7/14*   (2006.01)
(Continued)

(52) U.S. Cl.
CPC . *A47C 7/14* (2013.01); *A47C 1/023* (2013.01); *A47C 9/002* (2013.01); *A61F 5/00* (2013.01)

(58) Field of Classification Search
CPC ............ A47C 9/10; A47C 7/46; A47C 1/032; A47C 7/40; A47C 7/14; A47C 1/023
USPC ........ 297/299, 300.2, 300.6, 341, 342, 301.1, 297/317, 337
See application file for complete search history.

(56) References Cited

U.S. PATENT DOCUMENTS 5,354,120 A * 10/1994 Volkle .......................... 297/300.1
5,810,440 A *  9/1998 Unwalla ....................... 297/316
(Continued)

FOREIGN PATENT DOCUMENTS

WO   WO 0232262 A1 *  4/2002

*Primary Examiner* — Laurie Cranmer
(74) *Attorney, Agent, or Firm* — AKC Patents, LLC; Aliki K. Collins

(57) ABSTRACT

Provided is a corrective chair using a slider means that includes a supporting leg, a seat plate that is coupled to the supporting leg and on which a user seats, and a backrest whose lower part is coupled to an upper part of the supporting leg and that supports a back of the user when the user seats on the seat plate. The chair includes a slider that is interposed between the supporting leg and the seat plate. The slider includes guide rails that are coupled to both sides of a top surface of the supporting leg, and are disposed to be inclined toward the backrest in such a manner that portions of the guide rails close to the backrest are lowered and portions thereof opposite to the backrest are raised; guide blocks whose lower parts are slidably coupled to the guide rails, that are disposed on the guide rails opposite to the backrest in an initial state, and whose upper parts are coupled to a bottom surface of the seat plate; and elastic bodies whose one sides are coupled to a bottom surface of a front side of the seat plate and the other sides are coupled to a top surface of the supporting leg. When the user seats on the seat plate, the guide blocks are slid in an inclined direction of the guide rails to compress the elastic bodies, and the seat plate is moved toward the backrest to allow a back of the user to come in contact with the backrest, and when the user rises from the seat plate, the elastic bodies are restored to original states to restore the guide blocks and the seat plate to original states. Accordingly, since the guide rails are disposed to be inclined, when the user seats on the seat plate, the seat plate is retreated toward the backrest to allow the back of the user to come in close to the backrest. Accordingly, even though the user unconsciously seats on the chair, since the corrective chair using a slider means allows back portions of an upper body such as pelvis and waist to be straightened, the corrective chair using a slider means can correct a posture of the user so as to allow the user to seat on the chair in a correct posture.

1 Claim, 1 Drawing Sheet

(51) Int. Cl.
*A47C 1/023* (2006.01)
*A61F 5/00* (2006.01)
*A47C 9/00* (2006.01)

(56) References Cited

U.S. PATENT DOCUMENTS

| | | | |
|---|---|---|---|
| 6,824,219 B2 * | 11/2004 | Ruckstadter | 297/423.27 |
| 6,923,503 B2 * | 8/2005 | Sangiorgio | 297/342 |
| 8,864,230 B2 * | 10/2014 | Augustat | 297/300.2 |
| 2002/0171277 A1 * | 11/2002 | Bock | 297/300.2 |
| 2004/0051362 A1 * | 3/2004 | Heidmann et al. | 297/342 |
| 2006/0244294 A1 * | 11/2006 | Dozsa-Farkas | 297/300.2 |
| 2007/0222265 A1 * | 9/2007 | Machael et al. | 297/300.2 |
| 2010/0289309 A1 * | 11/2010 | Fich | 297/300.2 |
| 2012/0062005 A1 * | 3/2012 | Cvek | 297/284.4 |
| 2014/0084660 A1 * | 3/2014 | Norman et al. | 297/452.1 |

* cited by examiner

Horizontal ground

CORRECTIVE CHAIR USING SLIDER MEANS

CROSS-REFERENCE TO RELATED APPLICATIONS

This application is a National phase of PCT patent Application No. PCT/KR2012/008477 having International filing date of Oct. 17, 2012 which claims the benefit of priority of Korean Patent Application No. 10-2011-0107842 filed on Oct. 21, 2011. The contents of the above applications are all incorporated by reference as if fully set forth herein in their entirety.

TECHNICAL FIELD

The present invention relates to a corrective chair using a slider means, and more particularly, relates to a corrective chair using a slider means capable of effectively preventing musculoskeletal damage caused by an office chair.

BACKGROUND ART

In general, an office chair has a basic function for a user to sit at work, and also has a function as a space for waist protection and relaxation.

Most people including students or office workers spend substantial amount of time in their daily life in chairs. Thus, since a load of an upper body is transferred to a spine and pelvis, stress is applied to the spine, the pelvis and muscles around the spine and pelvis, so that people may suffer from a feeling of fatigue or pain.

Further, when people do not maintain a correct sitting posture due to an incorrect sitting posture or a badly designed chair, a spinal disk disorder (herniated lumbar disc) may be caused.

For this reason, a corrective chair capable of correcting the sitting posture to prevent the spinal disk disorder has been suggested, and the corrective chair that is often exposed in daily life is ergonomically designed. However, most corrective chairs according to the related art do not customize to the user, and the user may need to adjust the corrective chair when the user sits in the chair.

DISCLOSURE

Technical Problem

In order to solve the problems, an object of the present invention is to provide an improved corrective chair using a slider means capable of correcting a posture of a user in response to a weight of the user so as not to lose user's posture caused by user's habit when the user sits on the chair.

Technical Solution

In order to achieve the above object, an exemplary embodiment of the present invention provides a corrective chair using a slider means that includes a supporting leg, a seat plate that is coupled to the supporting leg and on which a user sits, and a backrest whose lower part is coupled to an upper part of the supporting leg and that supports a back of the user when the user sits on the seat plate. The chair includes a slider that is interposed between the supporting leg and the seat plate. The slider includes guide rails that are coupled to both sides of a top surface of the supporting leg, and are declined toward the backrest in such a manner that portions of the guide rails close to the backrest are lowered and portions thereof opposite to the backrest are raised; guide blocks whose lower parts are slidably coupled to the guide rails, that are disposed on the guide rails opposite to the backrest in an initial state, and whose upper parts are coupled to a bottom surface of the seat plate; and elastic bodies whose one sides are coupled to a bottom surface of a front side of the seat plate and the other sides are coupled to a top surface of the supporting leg. When the user sits on the seat plate, the guide blocks are configured to slide in a declined direction of the guide rails, the elastic bodies are compressed, and the seat plate is moved toward the backrest to allow a back of the user to come in contact with the backrest, and when the user rises from the seat plate, the elastic bodies are restored to original states to restore the guide blocks and the seat plate to original states.

Effect of the Invention

According to the corrective chair using a slider means of the present invention, since the guide rails are declined, when the user sits on the seat plate, the elastic bodies are compressed, and, thus, the seat plate is retreated toward the backrest to allow the back of the user to come in close to the backrest. Accordingly, even though the user unconsciously sits on the chair, since the corrective chair using a slider means allows back portions of an upper body such as pelvis and waist to be straightened, the corrective chair using a slider means can correct a posture of the user so as to allow the user to sit on the chair in a correct posture.

Further, when the user rises from the seat plate, the elastic bodies are restored to original states to restore the seat plate to its initial state.

BEST MODE

Hereinafter, a corrective chair using a slider means of the present invention will be described in detail with reference to the accompanying drawings.

Figure 1:
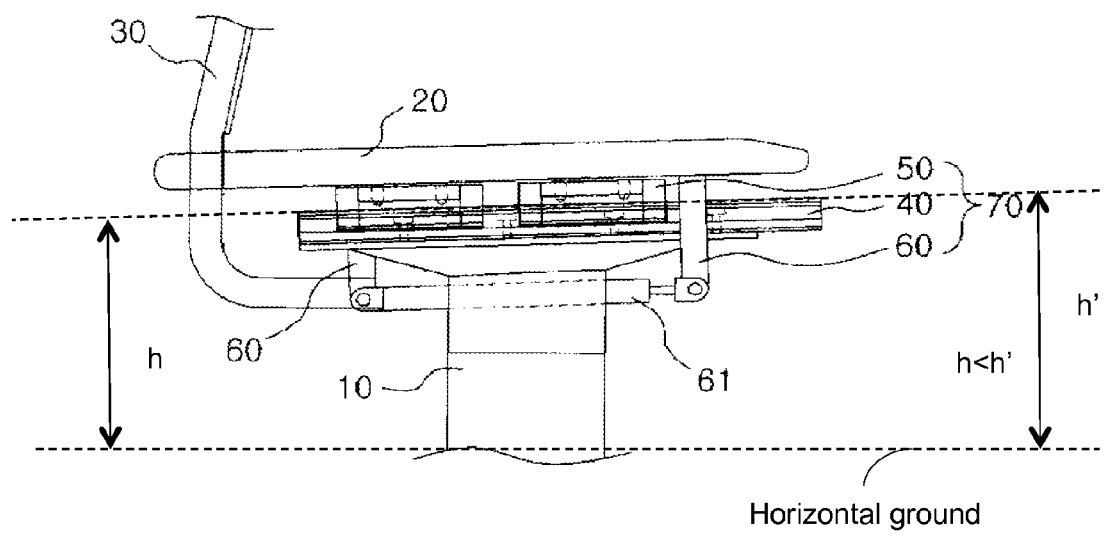
FIG. 1 is a schematic side view of a corrective chair using a slider means according to an embodiment of the present invention.
Figure 2:
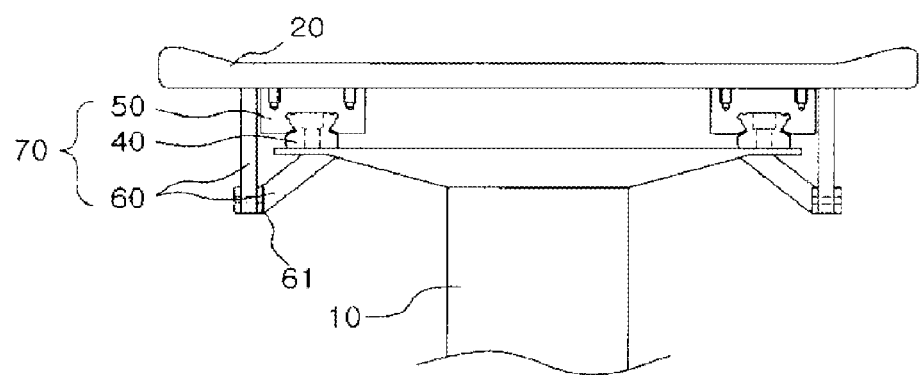
FIG. 2 is a schematic front view of the corrective chair using a slider means of FIG. 1.

FIG. 1 is a schematic side view of a corrective chair using a slider means according to an embodiment of the present invention, and FIG. 2 is a schematic front view of the corrective chair using a slider means of FIG. 1.

Referring to FIGS. 1 and 2, the corrective chair using a slider means of the present invention includes a supporting leg 10, a seat plate 20 that is coupled to the supporting leg 10 and on which a user sits, a backrest 30 that is coupled to the supporting leg 10 to support a back of the user sitting on the seat plate 20, and a slider 70 that is interposed between the supporting leg 10 and the seat plate 20.

The slider 70 includes guide rails 40, guide blocks 50, and elastic bodies 60.

A pair of guide rails 40 is respectively coupled to both sides of a top surface of the supporting leg 10. The guide rails are declined toward the backrest 30 in such a manner that portions of the guide rail close to the backrest 30 are lowered and portion thereof opposite to the backrest 30 are raised. The rails are inclined such that when a ball is placed on a side of the seat plate 20 opposite to the backrest 30, the ball naturally rolls toward the backrest 30 by gravity.

Lower parts of the guide blocks 50 are slidably coupled to the guide rail 40, and top surfaces thereof are coupled to a bottom surface of the seat plate 20.

A plurality of guide blocks 50 is provided. For example, two guide blocks 50 may be coupled to one guide rail 40, and two guide blocks 50 may be coupled to the other guide rail 40.

The elastic body 60 is a shover or a spring, and lower ends of a pair of elastic bodies 60 that are spaced apart from each other are coupled by a connection bar 61. One ends thereof are coupled to the bottom surface of the seat plate 20, and the other ends thereof are coupled to an upper part of the supporting leg 10.

Here, one elastic body 60 is coupled to a front side of the seat plate 20, that is, a side opposite to the backrest 30, and the other elastic body is coupled to the supporting leg 10 close to the backrest 30.

According to the corrective chair using a slider means having the aforementioned structure, the user sits on the seat plate 20 to compress the elastic bodies 60, the guide blocks 50 are slid on the guide rails 40 toward the backrest 30, and the seat plate 20 coupled to the guide blocks 50 is also slid toward the backrest 30. Thus, the back of the user comes in close contact with the backrest 30, and when the user rises from the seat plate 20, the elastic bodies 60, the guide blocks 50 and the seat plate 20 are restored to their original states.

According to the corrective chair using a slider means having the aforementioned structure, since the guide rails 40 are declined, when the user sits on the seat plate 20, the seat plate 20 retracts toward the backrest 30 to allow the back of the user to come in close to the backrest 30. Accordingly, even though the user unconsciously sits on the chair, since the corrective chair using a slider means allows back portions of an upper body such as pelvis and waist to be straightened, the corrective chair using a slider means can correct a posture of the user so as to allow the user to sit on the chair in a correct posture.

The invention claimed is:

1. A corrective chair using a slider means that includes a supporting leg, a seat plate that is coupled to the supporting leg and on which a user sits, and a backrest whose lower part is coupled to an upper part of the supporting leg and that supports a back of the user when the user sits on the seat plate, the chair comprising:
    a slider that is interposed between the supporting leg and the seat plate, wherein the slider includes:
    guide rails that are coupled to both sides of a top surface of the supporting leg, and are declined toward the backrest in such a manner that portions of the guide rails close to the backrest are lowered and portions thereof opposite to the backrest are raised;
    guide blocks whose lower parts are slidably coupled to the guide rails, that are disposed on the guide rails opposite to the backrest in an initial state, and whose upper parts are coupled to a bottom surface of the seat plate; and
    elastic bodies whose one sides are coupled to a bottom surface of a front side of the seat plate and the other sides are coupled to a top surface of the supporting leg,
    wherein when the user sits on the seat plate, the guide blocks are slid in a declined direction of the guide rails and the elastic bodies are compressed, and the seat plate is moved toward the backrest to allow a back of the user to come in contact with the backrest, and
    when the user rises from the seat plate, the elastic bodies are restored to original states to restore the guide blocks and the seat plate to original states.

* * * * *